United States Patent
Falkner et al.

(10) Patent No.: US 11,058,394 B2
(45) Date of Patent: Jul. 13, 2021

(54) STETHOSCOPE

(71) Applicants: Frankie Wendell Erdman, Jr., Fairhope, AL (US); Cunningham Bounds, LLC, Mobile, AL (US)

(72) Inventors: Carla W. Falkner, Mobile, AL (US); Deneen T. Plessala, Mobile, AL (US); Clifford A. Henricksen, Framingham, MA (US)

(73) Assignees: Frankie Wendell Erdman, Jr., Fairhope, AL (US); Cunningham Bounds, LLC, Mobile, AL (US)

( * ) Notice: Subject to any disclaimer, the term of this patent is extended or adjusted under 35 U.S.C. 154(b) by 41 days.

(21) Appl. No.: 16/389,637

(22) Filed: Apr. 19, 2019

(65) Prior Publication Data

US 2019/0239847 A1     Aug. 8, 2019

Related U.S. Application Data

(60) Division of application No. 16/152,706, filed on Oct. 5, 2018, now Pat. No. 10,292,675, which is a
(Continued)

(51) Int. Cl.
*A61B 7/02* (2006.01)
*H04R 1/46* (2006.01)
(Continued)

(52) U.S. Cl.
CPC .............. *A61B 7/02* (2013.01); *A61B 7/003* (2013.01); *H04R 1/46* (2013.01)

(58) Field of Classification Search
CPC ........... A61B 7/02; A61B 7/026; A61B 7/001; A61B 7/003; A61B 7/005; A61B 7/006;
(Continued)

(56) References Cited

U.S. PATENT DOCUMENTS

| 1,657,078 A | 1/1928 | Frederick |
| 3,020,971 A | 2/1962 | Cefaly |

(Continued)

FOREIGN PATENT DOCUMENTS

| CN | 2862969 Y | 1/2007 |
| CN | 101172039 A | 5/2008 |

(Continued)

OTHER PUBLICATIONS

Medeiros Gaspar, Ana; International Search Report by International Search Authority (European Patent Office) for PCT/US2018/030807. (Year: 2018).*

(Continued)

*Primary Examiner* — Edgardo San Martin
(74) *Attorney, Agent, or Firm* — Millen, White, Zelano & Branigan, PC; Ryan Pool

(57) ABSTRACT

A stethoscope with a body and a diaphragm comprising a flexible enclosure containing an incompressible liquid suspended in the stethoscope body with a reticulated foam pressure pad located below the diaphragm and inside an inner perimeter of the body. Optionally, the diaphragm has a cap over a top end of the suspended flexible enclosure, preferably made from copper in order to provide antimicrobial properties.

9 Claims, 10 Drawing Sheets

Related U.S. Application Data continuation of application No. PCT/US2018/030807, filed on May 3, 2018.

(60) Provisional application No. 62/645,553, filed on Mar. 20, 2018, provisional application No. 62/570,302, filed on Oct. 10, 2017.

(51) Int. Cl.
 *A61B 7/00* (2006.01)
 *H04R 1/42* (2006.01)

(58) Field of Classification Search
 CPC ........... A61B 7/008; A61B 7/04; A61B 7/045; H04R 1/46; H04R 1/42
 See application file for complete search history.

(56) References Cited

U.S. PATENT DOCUMENTS

| | | | |
|---|---|---|---|
| 3,109,508 A | 11/1963 | Cefaly | |
| 3,130,275 A * | 4/1964 | Hagey | H04R 17/02 381/166 |
| 3,179,204 A | 4/1965 | Cefaly | |
| 3,239,696 A * | 3/1966 | Burkhalter | A61B 5/022 310/327 |
| 3,472,336 A | 10/1969 | Dahl | |
| 3,867,925 A | 2/1975 | Ersek | |
| 4,409,681 A * | 10/1983 | White | G10K 9/121 367/155 |
| 4,409,983 A | 10/1983 | Albert | |
| 4,440,258 A * | 4/1984 | Packard | A61B 7/02 181/137 |
| 4,561,447 A * | 12/1985 | Kawamura | A61B 5/021 600/500 |
| 4,640,295 A | 2/1987 | Isaacson | |
| 4,903,794 A | 2/1990 | Klippert et al. | |
| 5,335,210 A * | 8/1994 | Bernstein | G01H 11/06 367/163 |
| 5,424,495 A * | 6/1995 | Wurzburger | A61B 7/026 181/131 |
| 5,448,025 A * | 9/1995 | Stark | A61B 7/02 181/131 |
| 5,772,575 A * | 6/1998 | Lesinski | H04R 25/606 600/25 |
| 5,796,053 A | 8/1998 | Shieh | |
| 5,853,005 A * | 12/1998 | Scanlon | A61B 5/113 600/459 |
| 5,931,792 A | 8/1999 | Packard et al. | |
| 6,068,589 A * | 5/2000 | Neukermans | H04R 17/00 600/25 |
| 6,295,365 B1 * | 9/2001 | Ota | H04R 17/00 381/114 |
| 6,438,238 B1 | 4/2002 | Callahan | |
| 6,491,647 B1 | 12/2002 | Bridger et al. | |
| 6,726,635 B1 | 4/2004 | LaSala | |
| 7,806,226 B2 | 10/2010 | Drummond et al. | |
| 8,615,285 B2 * | 12/2013 | Ehman | G01R 33/56358 600/411 |
| 9,101,274 B2 * | 8/2015 | Bakema | A61B 7/04 |
| 9,591,413 B2 * | 3/2017 | Miller | H04R 25/604 |
| 10,076,251 B2 | 9/2018 | Tu et al. | |
| 10,292,675 B2 * | 5/2019 | Falkner | A61B 7/02 |
| 10,765,871 B2 * | 9/2020 | Kane | A61B 5/0215 |
| 2006/0227979 A1 | 10/2006 | Chen | |
| 2008/0166384 A1 * | 7/2008 | Jones | A01N 25/34 424/402 |
| 2010/0094152 A1 * | 4/2010 | Semmlow | A61B 7/00 600/528 |

FOREIGN PATENT DOCUMENTS

| | | |
|---|---|---|
| CN | 201253219 Y | 6/2009 |
| CN | 101647712 A | 2/2010 |
| RU | 128693 U1 | 5/2013 |
| SU | 260080 A | 12/1969 |
| WO | 19074543 A1 | 4/2019 |

OTHER PUBLICATIONS

Medeiros Gaspar, Ana; Written Opinion by International Search Authority (European Patent Office) for PCT/US2018/030807. (Year: 2018).*

Notification of Reasons for Refusal in corresponding KR application 9-5-2020-050403505 dated Jul. 24, 2020 (pp. 1-4) and English translation thereof (pp. 1-3).

International Search report PCT/US2018/30807 dated Apr. 14, 2020 (pp. 1-7).

Office Action in corresponding Russian application No. 2020113272/14(022406) dated Nov. 19, 2020 (pp. 1-8).

First Office Action in corresponding China Application No. 201880066427.8 dated Mar. 17, 2021 (pp. 1-7) and English translation thereof (pp. 1-5).

* cited by examiner

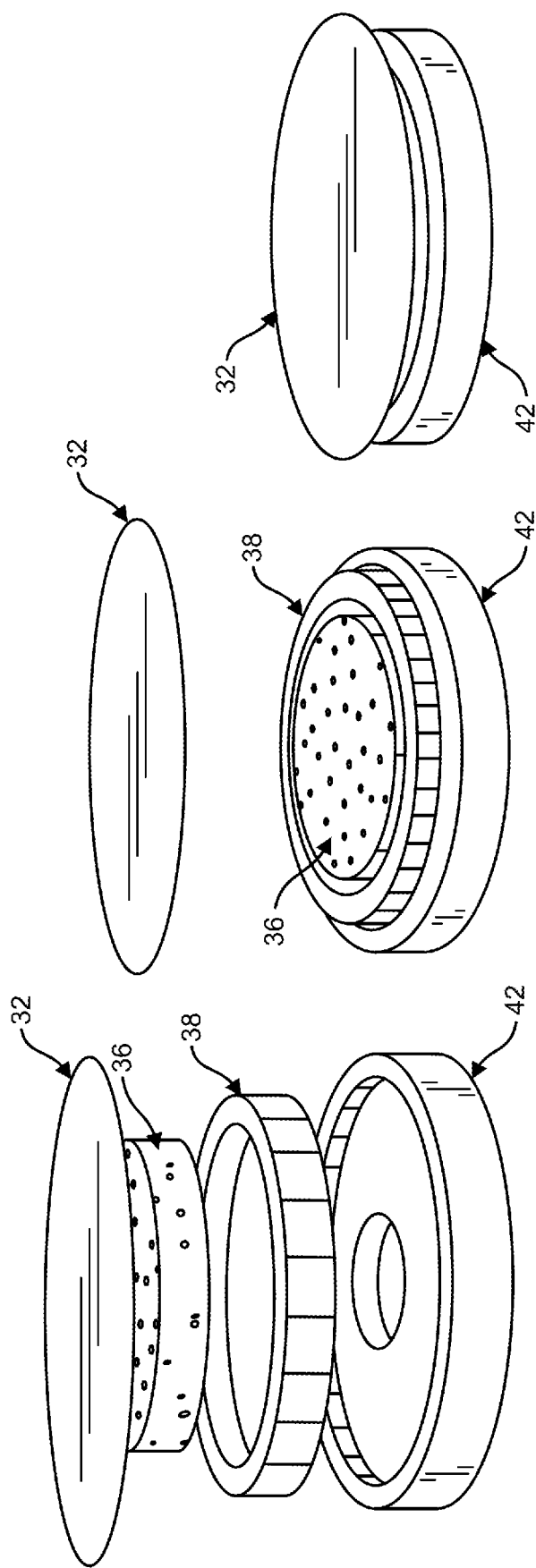

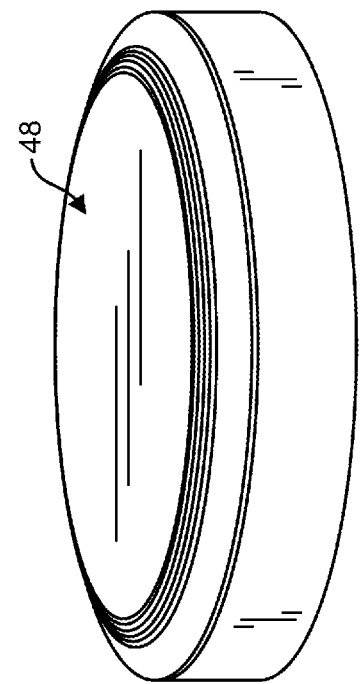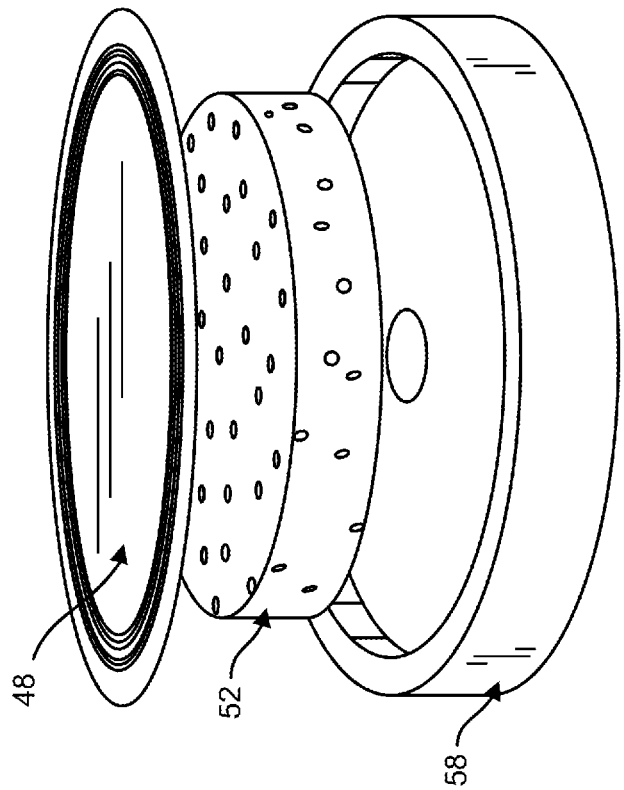

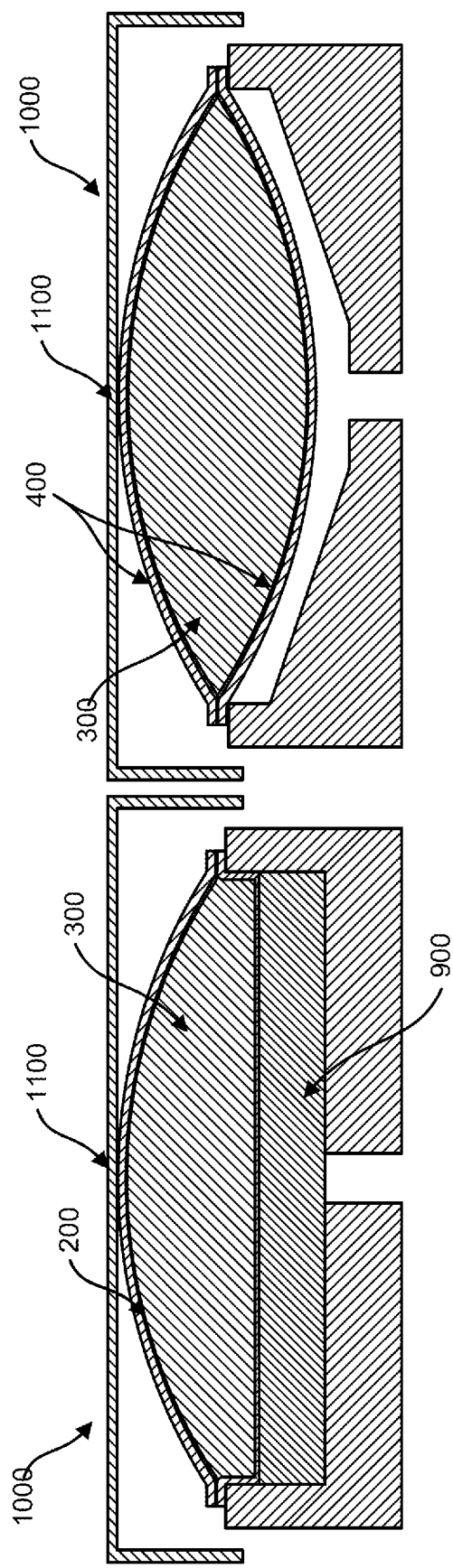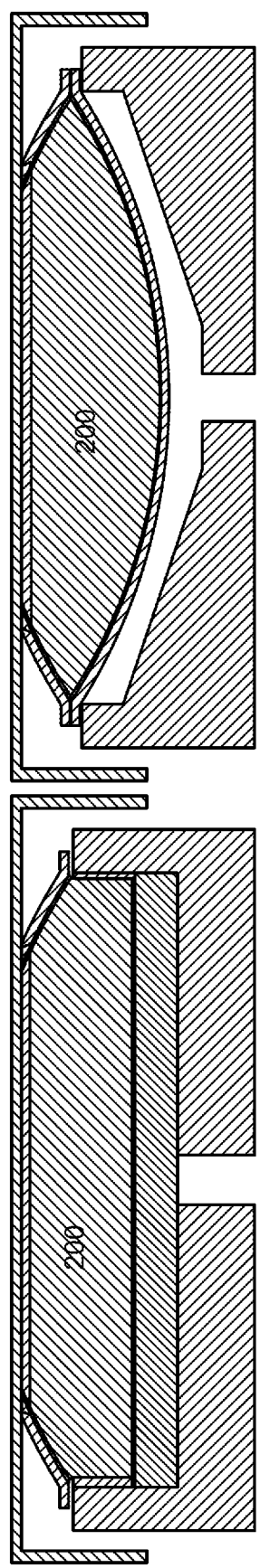

STETHOSCOPE

RELATED APPLICATIONS

This application is a divisional of U.S. application Ser. No. 16/152,706, filed Oct. 5, 2018, which is a continuation of International Application No. PCT/US2018/030807, filed May 3, 2018, which claims the benefit of U.S. Provisional Application Nos. 62/570,302 filed Oct. 10, 2017 and 62/645,553 filed Mar. 20, 2018. The entire contents of the above applications are hereby incorporated by reference as though fully set forth herein.

BACKGROUND

A stethoscope is used to amplify body-borne sounds sent from a human or animal heart, lung, stomach, etc., as a means of diagnosis. Using a stethoscope, the listener can hear normal and abnormal respiratory, cardiac, pleural, arterial, venous, uterine, fetal and intestinal sounds. Most stethoscopes have the following parts: eartips, eartube, tubing, headset, stem, chest-piece, diaphragm, and a bell. Sounds from the body are passively amplified and transmitted to an air volume via the bell or a diaphragm. The diaphragm mechanism is preferred for most diagnostic applications.

The diaphragm is normally a thin structure typically made of flat or curvilinear-formed plastic material with some means of creating axial compliance so that it can have motion. When the diaphragm is pressed to the patient's flesh, it will move due to body-generated pressures. The diaphragm is air-sealed to an enclosed or captive air volume which has a small hole in it leading to air tubes. The diaphragm's motion changes the volume of captive air, thus creating an acoustic signal at the exit hole that enters the air tubes. The resulting acoustic signals are then sent via the tube assembly to the stethoscope operator's ears.

There have been numerous studies that indicate that stethoscopes transmit infectious agents between patients and are a source of healthcare associated infections.[1] Many show that the contamination level of the stethoscope is substantial after a single physical examination. While healthcare workers are mandated to wash or otherwise sanitize their hands after patient contact, there are currently no guidelines that require stethoscopes be sanitized after every use. The diaphragm is the part of the stethoscope that maintains the most contact with the patient. As such, it would be useful for stethoscope diaphragms to be constructed from materials that are known to be antimicrobial in nature, such as copper and copper alloys, and still retain their acoustic-transduction properties.

[1] https://www.+news-medical.ne-Vne.vs/20170511+:New-study-reveals-8025-of-stethoscopes-are-contaminated-with-infectious-bacteria.aspx (accessed Mar. 1, 2018) (discussing a study performed by the American Journal of Infection Control revealing that "80 percent of the stethoscopes they studied were contaminated by high concentrations of bacteria.")

BRIEF SUMMARY OF THE INVENTION

In a first embodiment, the present invention is a stethoscope with a body; a diaphragm; and an integral annular axially compliant suspension. The annular axially compliant suspension fits under the diaphragm and inside an inner perimeter of the body. In the preferred embodiment, a reticulated foam pressure pad with an annular suspension is sealed on the interior or outer diameter of the body. In an additional embodiment, the diaphragm is comprised of a very thin foil, preferably made from copper in order to provide antimicrobial properties.

In a second embodiment, the present invention is a stethoscope with a body and a diaphragm comprised of a flexible enclosure containing an incompressible liquid suspended in the stethoscope body. In the preferred embodiment, a reticulated foam pressure pad with an annular suspension is sealed on the interior or outer diameter of the body. In an additional embodiment, the diaphragm has a cap over a top end of the suspended flexible enclosure, preferably made from copper in order to provide antimicrobial properties.

BRIEF DESCRIPTION OF THE DRAWINGS

FIG. 4 is a perspective exploded view of an exemplary embodiment of a planar diaphragm with integral annular outer-suspension and reticulated-foam pressure pad.

FIG. 5 is a perspective view of an exemplary embodiment of a planar diaphragm with integral annular outer-suspension and reticulated-foam pressure pad with the diaphragm removed.

FIG. 6 is a perspective view of an exemplary embodiment of a planar diaphragm with integral annular outer-suspension and reticulated-foam pressure pad with the diaphragm attached.

FIG. 7 is a perspective view of the annular bellow suspension of a planar diaphragm.

FIG. 8 is an exploded perspective view of an exemplary embodiment of a planar diaphragm with annular bellow suspension and internal pressure pad.

FIG. 9 is a side perspective view of an exemplary embodiment of a planar diaphragm with annular bellow suspension and internal pressure pad.

FIG. 14A contains cross-sectional views of the stethoscope head of FIG. 12 with the additional antimicrobial cap.

FIG. 14B contains cross-sectional views of the stethoscope head of FIG. 10 with the additional antimicrobial cap.

FIG. 14C contains cross-sectional views of the stethoscope head of FIG. 13 with the additional antimicrobial cap when in use.

FIG. 14D contains cross-sectional views of the stethoscope head of FIG. 11 with the additional antimicrobial cap when in use.

DETAILED DESCRIPTION

Figure 15:
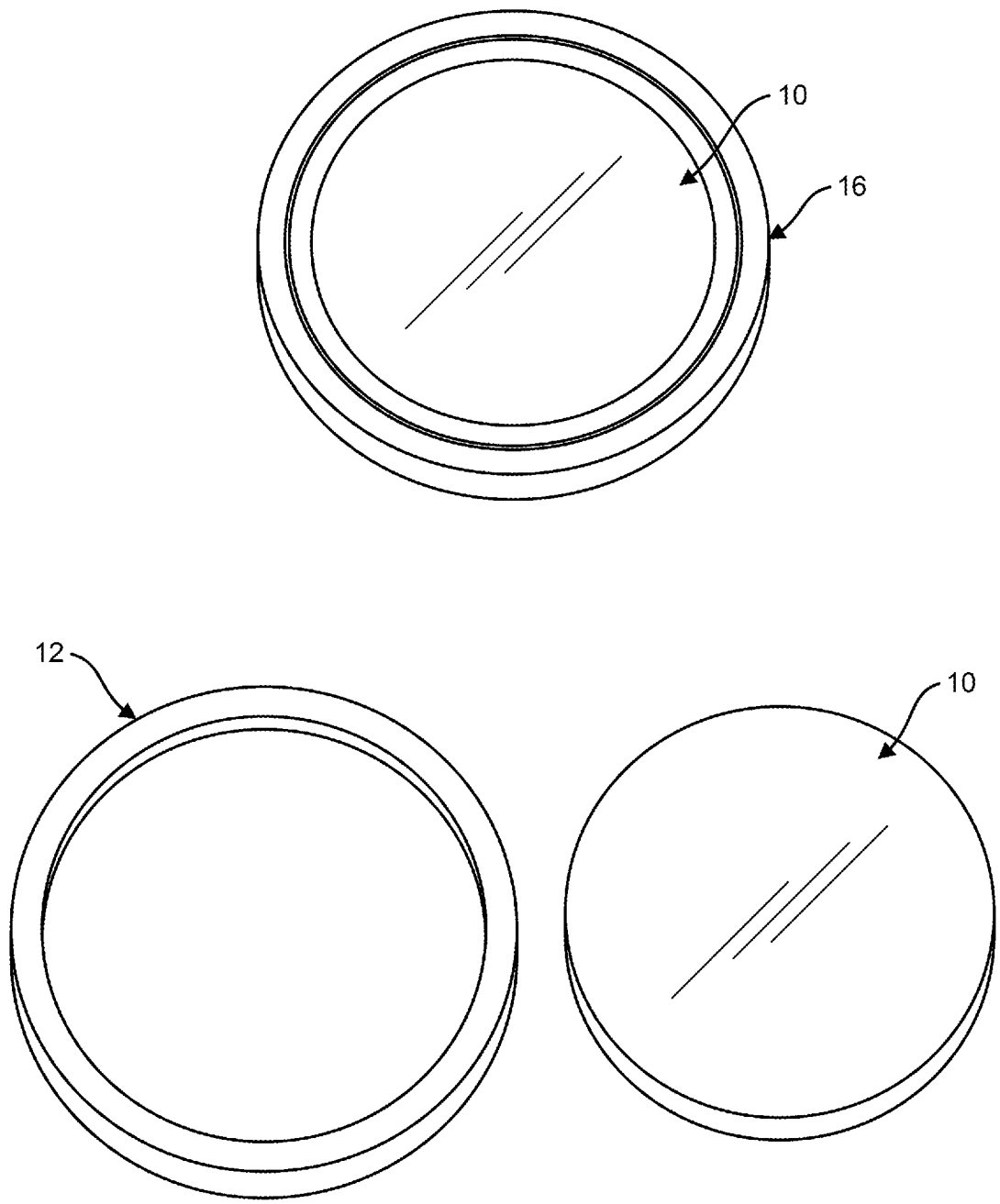
FIG. 15 is a top view of a first version of a diaphragm inside a viscoelastic annular suspension ring and a urethane holding rim used in a stethoscope of the prior art.

Turning to FIG. 15, the typical stethoscope of the prior art is shown where the stethoscope diaphragm is held in place to the stethoscope body by the ring 12, which has a matching thread-closure. The ring 12 generally comprises a viscoelastic annular suspension that surrounds the diaphragm 10 as a means of improving its ability to move in concert with body vibrations. The diaphragm 10 and the ring 12 are then positioned within the stethoscope body and sealed with a urethane rim 16 that fits around the ring 12 and body assembly. The diaphragm 10 could be made of anti-microbial copper, but in order to be effective in preventing the transmission of bacteria, the diaphragm 10 as well as the ring 12 and urethane rim 16 would also need to be made of copper since all of these components contact the patient's skin. But, if the ring 12 is made of stiffer copper, the diaphragm 10 would be unable to vibrate and the stethoscope would not work. Additionally, the crevices created between the diaphragm 10 and the ring 12 or the ring 12 and the rim 16 facilitate the transmission of bacteria if the entire surface is not flush and made with an antimicrobial material, such as copper.

In order to utilize the antimicrobial properties of copper and copper alloys, it becomes important to suspend the diaphragm with a suspension element that does not come in contact with the patient; an axially-compliant element under and at the outer perimeter of the copper diaphragm is the preferred embodiment to meet this requirement. The more compliant the suspension, the more output is suspected. Additionally, a back-chamber behind the diaphragm must be air-sealed at all its internal boundaries including those of any suspension element. The smaller the volume of the back-chamber, the more high-frequency output is expected (as is the case in electrodynamic "compression driver" loudspeakers).

The back chamber should be fitted with a small exit port, which is in turn connected to air tubes. These tubes carry the acoustic signals generated by the motion of the diaphragm to the user's ears.

Also, a larger diaphragm and a smaller feed-exit, relative to the size of the diaphragm results in higher sensitivity. The ratio of diaphragm area to feed-exit area will henceforth be called the "compression ratio" of the stethoscope.

An advanced design employs multiple small feed exits (in the back chamber) that are in turn manifolded into a single main exit port to improve the smoothness of the high-frequency output of the stethoscope. With a single feed-exit, a series of dips and bumps in output (harmonically related) occur.

Several embodiments are disclosed herein that meet these aforementioned design requirements.

Figure 2:
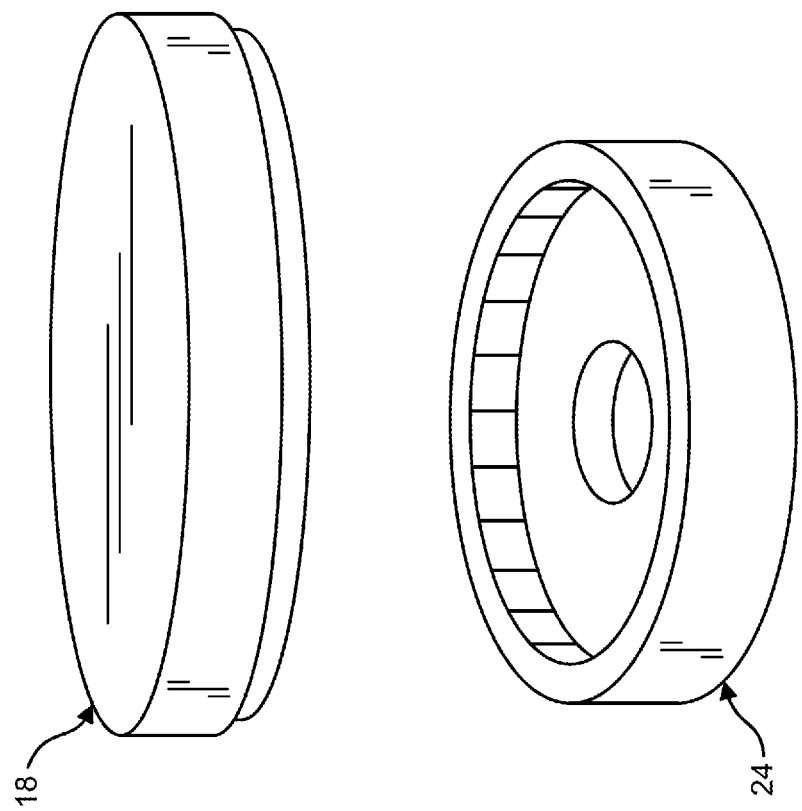
FIG. 2 is an exploded perspective view of an exemplary embodiment of the exterior portions of a simple planar/cup diaphragm with annular sealed foamed suspension of the present invention.
Figure 1:
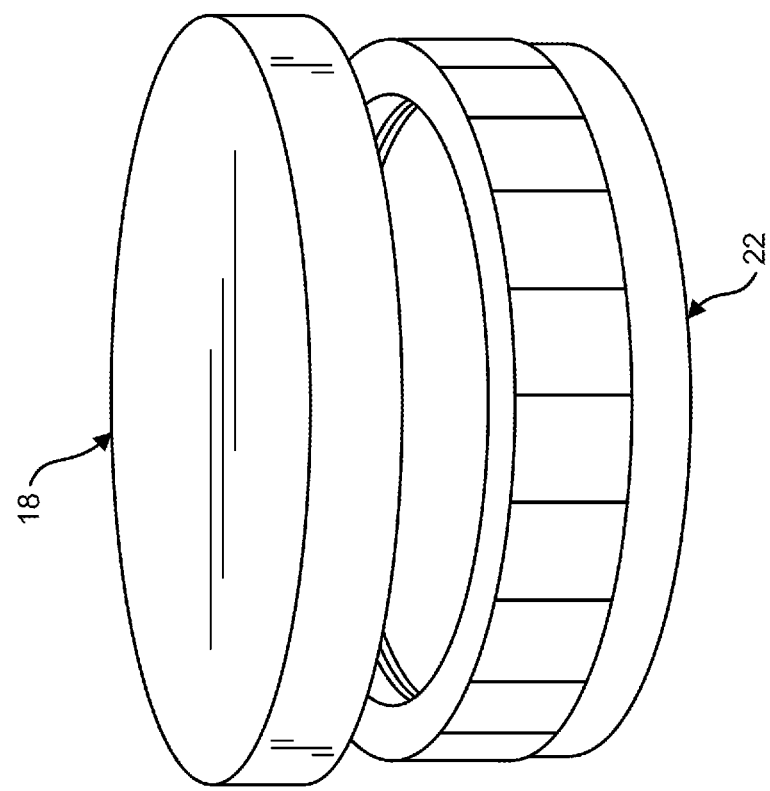
FIG. 1 is an exploded perspective view of an exemplary embodiment of the interior portion of a simple planar/cup diaphragm with annular sealed foamed suspension of the present invention.

Turning to FIG. 2, in a first design, a simple planar or cup-shaped diaphragm 18 has annular closed cell foamed suspension wherein the foam 22 of the foamed suspension is sealed in the stethoscope body 24 with highly compliant coating on the foamed suspension interior diameter or outer diameter. The foamed suspension is axially compliant.

Figure 3:
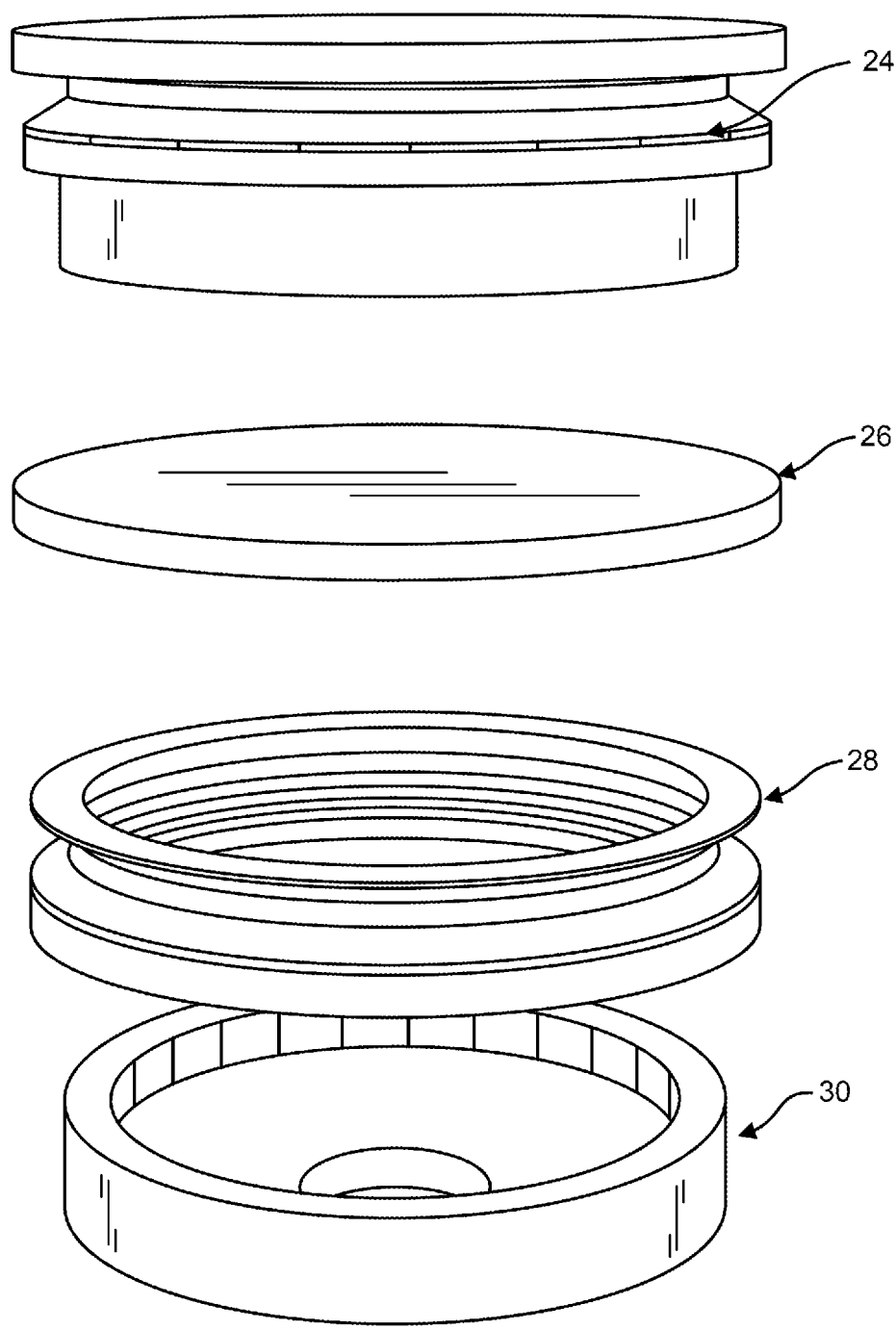
FIG. 3 is a side exploded view of an exemplary embodiment of a simple planar/cup diaphragm with axial elastomeric bellows suspension.

Turning to FIG. 3, in a second design, the simple planar or cup-shaped diaphragm 26 of FIG. 2 uses an axially compliant elastomeric (e.g. rubber) bellows suspension 28 sealed in the stethoscope body 30.

Turning to FIG. 4-6, in a third design, a planar diaphragm 32 with integral annular outer suspension and reticulated-foam pressure pad 36 has an annular suspension 38 sealed on the interior diameter or outer diameter in the stethoscope head 42 with compliant, viscoelastic coating. The pressure pad 36 is made of reticulated foam. The free-air pressure pad 36 extends the effective area of a thin-foil diaphragm 32 by pressing the diaphragm against the skin of the patient. Reticulated foam is preferred for the pressure pad as it is an elastomer that has open cells so it can act as a compliant element but also allow sound to pass through it unimpeded. Closed-cell foams are compliant but will block sound because they have closed "windows."

Turning to FIGS. 7-9, in a fourth embodiment, a planar diaphragm 48 with integral annular suspension 50 inside the stethoscope head 58 and internal pressure pad 52 (reticulated foam) has a formed-foil (or other material) diaphragm 48 with circumferential, annular corrugations that allow freedom of axial motion of the diaphragm. This is similar to suspensions of loudspeaker diaphragms. If the diaphragm 48 were made of very thin foil (copper or other), the pressure pad 52 would improve motion of the entire diaphragm surface by pressing it against the patient's skin.

In the preferred embodiment, as depicted in FIGS. 4-6, the stethoscope of the present invention, the stethoscope body 30 is an axisymmetric structure of a rigid material (e.g. aluminum, or other suitable light-weight metal or metal alloy) with a sound port in the back of the stethoscope body 30 feeding the output port radially. The stethoscope body 30 is about 3.2 inches outer diameter, giving an effective diaphragm 32 of about 2.6 inches outer diameter. The preferred foam suspension of the pushpad 36 is very compliant foam rubber that is closed-cell. The pushpad 36 is air-sealed on the inner diameter of the annular suspension 38 with a substantially viscoelastic coating applied with a brush. Preferentially, the annular suspension 38 is bonded to the stethoscope body 30 first, then coated on the inner diameter with the viscoelastic coating. The final step is an application of adhesive to the top of the annual suspension 38, then squeeze the diaphragm 32 down, thus compressing the diaphragm 32 onto the adhesive/suspension 38 along with the pushpad 36, which is spot-bonded to the stethoscope body 30 to keep it centered.

The pushpad 36 holds the diaphragm 32 taut because it is thicker than the suspension ring 38. The pushpad 36 is reticulated with a plurality of spaces and no closed cells, so it springs evenly against the diaphragm 32 but allows full airflow and sound generation into the center port of the stethoscope body 30. In the preferred embodiment, the diaphragm-to-body spacing along the main boundaries of the back-chamber is important, with the smaller the space resulting in better stethoscope performance. Further, the pushpad 36 is an important aspect of the present invention as a thin foil diaphragm 32 on its own would never be able to contact the skin uniformly, which in turn results in the internal pressure waves moving the diaphragm uniformly.

It is important to note that a thin foil diaphragm is superior as a rigid diaphragm (such as the typical formed "cup" diaphragm with a spherical-like surface that contacts the skin) does not conform to skin irregularities because it is a rigid three-dimensional structure.

In an alternative embodiment, a copper/copper alloy thin foil diaphragm with a solid annular outer suspension (as opposed to a compliant outer suspension) comprised of a raised outer ridge on the stethoscope body with the foil diaphragm bonded thereto is also functional as a stethoscope with antimicrobial properties for the diaphragm.

Figure 10:
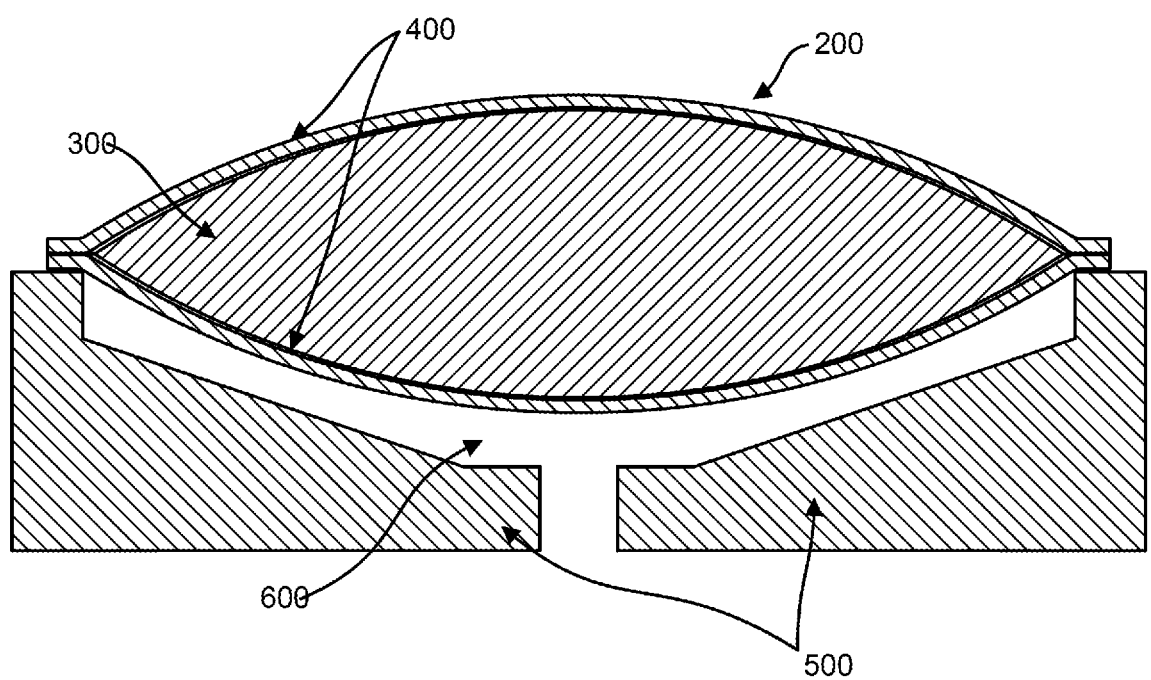
FIG. 10 is a cross-sectional view of the stethoscope head with a suspended sealed flexible enclosure containing an incompressible liquid while not in use.

Turning to FIG. 10, in an alternative embodiment, the diaphragm comprises a suspended flexible enclosure 200 that contains an incompressible liquid 300 (e.g. water or a saline solution) that is completely sealed by a non-permeable membrane 400. In the preferred embodiment, the membrane 400 is composed of a flexible material, like an elastomer or rubber. The diaphragm is suspended in a solid body 500 that creates an air cavity 600 between the body 500 and the diaphragm. The cavity 600 allows the diaphragm to freely flex downward into the cavity 600 when the diaphragm is pressed against a patient's skin 700 (as shown in FIG. 11).

Figure 11:
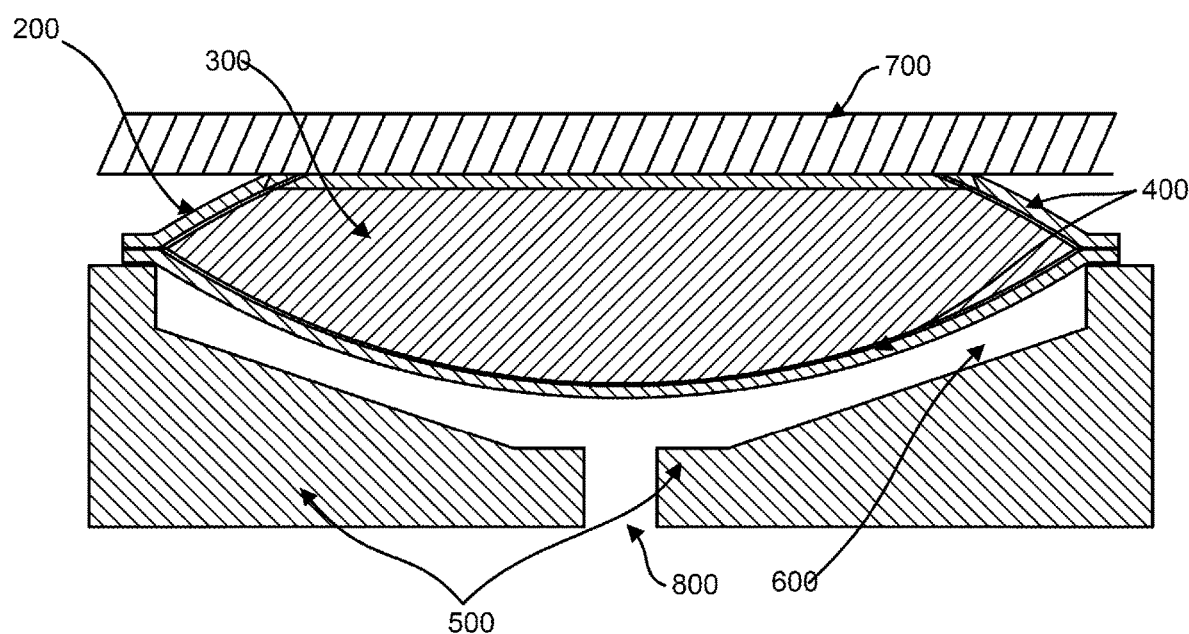
FIG. 11 is a cross-sectional view of the stethoscope head of FIG. 10 when the diaphragm is applied to the patient's skin.

Turning to FIG. 11, when the stethoscope is pressed against the patient's skin 700, body-borne pressure is applied to the diaphragm causing the sealed flexible enclosure 200 to fill the cavity 600 and reduce the air volume in the cavity 600; the result is a higher frequency output being generated and directed to the hearing-tube assembly through the exit portal 800 at the bottom of the cavity 600.

Figure 12:
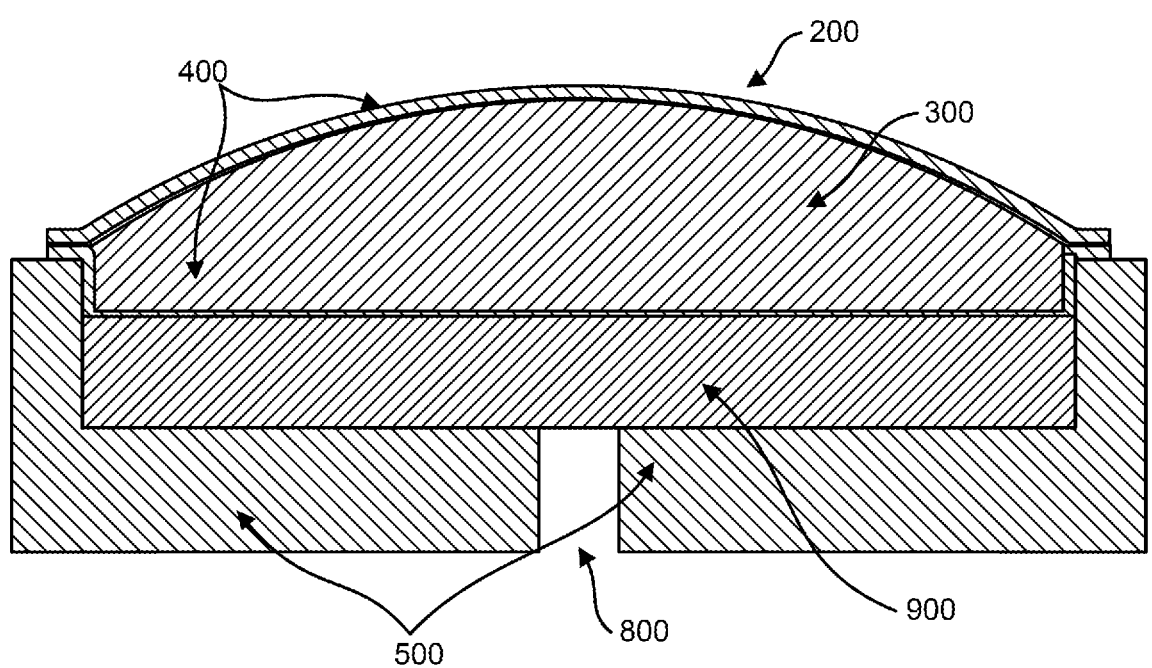
FIG. 12 is a cross-sectional view of the stethoscope head with a sealed flexible enclosure containing an incompressible liquid that is suspended above the stethoscope body by a pressure pad while not in use.

Turning to FIG. 12, in another embodiment, the diaphragm comprises a similarly sealed flexible enclosure 200 containing an incompressible liquid 300 that is suspended above the stethoscope body 500 by a pressure pad 900 with an annular suspension sealed on the interior or outer diameter of the body. In the preferred embodiment, the pressure pad 900 is constructed from reticulated foam, such as "Scottfoam" or any other reticulated foam product known in the art. The free-air pressure pad 900 substantially fills the cavity between the stethoscope body 500 and the sealed flexible enclosure 200. The pressure pad 900 is reticulated with a plurality of spaces and no closed cells, so it springs evenly against the sealed flexible enclosure 200 but allows virtually unimpeded airflow and sound generation into the exit portal 800 at the bottom of the stethoscope body 500.

Figure 13:
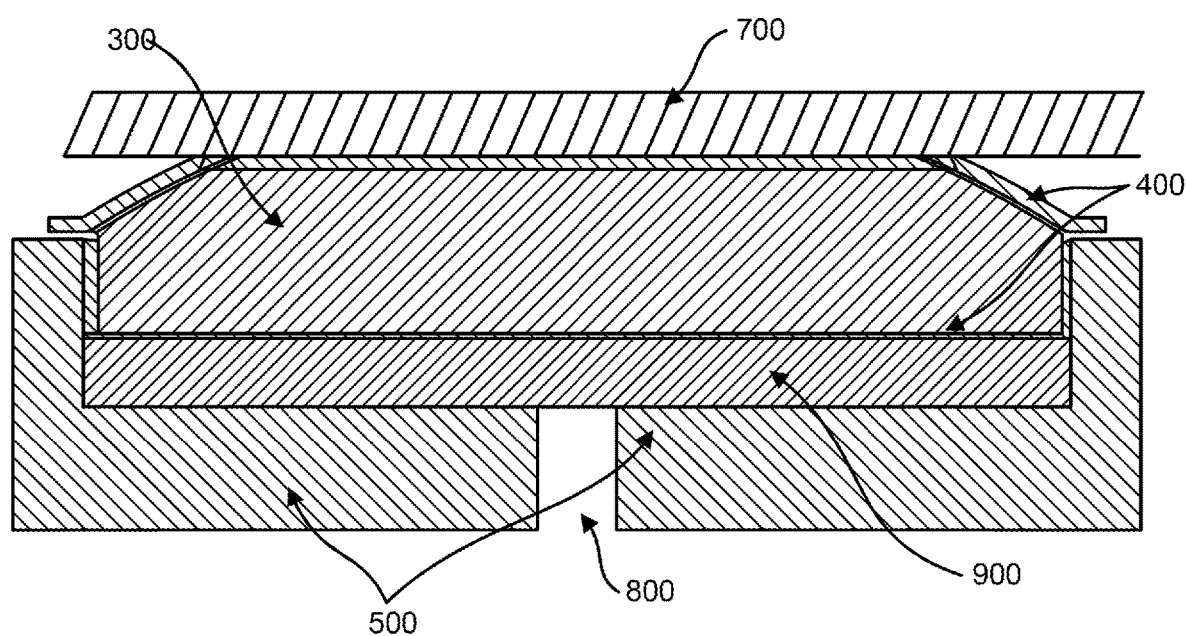
FIG. 13 is a cross-sectional view of the stethoscope head with a sealed flexible enclosure containing an incompressible liquid that is suspended above the stethoscope body by a pressure pad when the diaphragm is applied to the patient's skin.

As seen in FIG. 13, when body-borne pressure is applied to the sealed flexible enclosure 200, the incompressible liquid 300 in the sealed flexible enclosure 200 will naturally push against the pressure pad 900, thus minimizing the volume of air consumed by the pressure pad 900 and resulting in a higher sound output at the exit portal 800.

In both FIGS. 10 and 12, the stethoscope body 500 comprises an axisymmetric structure (e.g. a disc) of a solid, rigid material (e.g. metal, metal alloy, or plastic), with a sound port 800 in the back of the stethoscope body feeding the output port radially.

As seen in FIGS. 14A-D, a copper or other rigid material "cap" 1000 may be bonded to a small area at the center 1100 of the sealed flexible enclosure 200; this can be accomplished by any form of adhesive-bonding or other means of attachment known in the art. This centrally located attachment 1100 allows the cap 1000 to freely "wobble" on its vertical axis. When the sealed flexible enclosure 200 is pressed against the patient's skin 700, the compliant sealed flexible enclosure 200 conforms to the underside of the cap 1000, resulting in a low-impedance contact with the cap. The cap itself becomes the forcing member, directly driven by the body-borne pressure waves.

Additionally, the use of a liquid-based and flexible enclosure 200 in both embodiments has shown verifiable improvement in transduction. When pressed against the skin as shown in FIGS. 14 C-D, the flexible enclosure 200 essentially becomes an extension of the body in terms of structure—forming an intimate hydrodynamic connection to the body, via this skin interface that allows pressure waves to be received more efficiently. As a result, the acoustic impedance matching between the human body and the stethoscope is greatly improved over its mechanical counterpart known in the prior art.

For the purposes of promoting an understanding of the principles of the invention, reference has been made to the preferred embodiments illustrated in the drawings, and specific language has been used to describe these embodiments. However, this specific language intends no limitation of the scope of the invention, and the invention should be construed to encompass all embodiments that would normally occur to one of ordinary skill in the art. The particular implementations shown and described herein are illustrative examples of the invention and are not intended to otherwise limit the scope of the invention in any way. For the sake of brevity, conventional aspects of the method (and components of the individual operating components of the method) may not be described in detail. Furthermore, the connecting lines, or connectors shown in the various figures presented are intended to represent exemplary functional relationships and/or physical or logical couplings between the various elements. It should be noted that many alternative or additional functional relationships, physical connections or logical connections might be present in a practical device. Moreover, no item or component is essential to the practice of the invention unless the element is specifically described as "essential" or "critical". Numerous modifications and adaptations will be readily apparent to those skilled in this art without departing from the spirit and scope of the present invention.

What is claimed is:

1. A stethoscope comprising:
   a. a body;
   b. a diaphragm comprised of a flexible enclosure containing an incompressible liquid suspended in the stethoscope body, and
   c. a reticulated foam pressure pad with an annular suspension is sealed on the interior of the body and is in direct contact the flexible enclosure containing an incompressible liquid and the inner perimeter of the body.

2. The stethoscope of claim 1 further comprising a cap over a top end of the suspended flexible enclosure.

3. The stethoscope of claim 2 wherein the cap is comprised of copper.

4. The stethoscope of claim 1 wherein the pressure pad has a compliant, viscoelastic coating.

5. The stethoscope of claim 1 further comprising a cap over a top end of the suspended flexible enclosure.

6. The stethoscope of claim 5 wherein the cap is comprised of copper.

7. The stethoscope of claim 1, wherein the incompressible liquid is water or saline solution.

8. A stethoscope comprising:
   a. a body; and
   b. a diaphragm comprised of a flexible enclosure containing an incompressible liquid suspended above the stethoscope body by a non-permeable membrane which is in direct contact with a reticulated foam pressure pad with an annular suspension.

9. The stethoscope of claim 8, wherein the reticulated foam pressure pad is reticulated with a plurality of spaces and no closed cells, suitable for allowing it to spring evenly against the flexible enclosure but also to allow virtually unimpeded airflow and sound generation into an exit portal positioned at the bottom of the stethoscope body.

* * * * *